United States Patent
Barata et al.

(10) Patent No.: US 9,044,513 B2
(45) Date of Patent: Jun. 2, 2015

(54) LARGE PARTICLE SIZE CRYSTALLISED MALTITOL POWDER, METHOD FOR PREPARING SAME AND APPLICATIONS THEREOF, PARTICULARLY IN CHOCOLATE PRODUCTION

(75) Inventors: Manuel Barata, Gonnehem (FR); Yves Le Bot, Wattignies (FR); Elsa Muller née Ostermann, Gonnehem (FR); Guillaume Ribadeau-Dumas, Verlinghem (FR)

(73) Assignee: ROQUETTE FRERES, Lestrem (FR)

( * ) Notice: Subject to any disclaimer, the term of this patent is extended or adjusted under 35 U.S.C. 154(b) by 756 days.

(21) Appl. No.: 12/918,854

(22) PCT Filed: Feb. 20, 2009

(86) PCT No.: PCT/FR2009/050276
§ 371 (c)(1),
(2), (4) Date: Aug. 23, 2010

(87) PCT Pub. No.: WO2009/112740
PCT Pub. Date: Sep. 17, 2009

(65) Prior Publication Data
US 2011/0294903 A1    Dec. 1, 2011

(30) Foreign Application Priority Data
Feb. 22, 2008  (FR) ..................... 08 51168

(51) Int. Cl.
| | | |
|---|---|---|
| A61K 47/00 | (2006.01) | |
| A61K 47/26 | (2006.01) | |
| A23G 1/40 | (2006.01) | |
| A23G 3/42 | (2006.01) | |
| A23G 4/10 | (2006.01) | |
| A23L 1/236 | (2006.01) | |
| A23L 1/307 | (2006.01) | |

(52) U.S. Cl.
CPC . *A61K 47/26* (2013.01); *A23G 1/40* (2013.01); *A23G 3/42* (2013.01); *A23G 4/10* (2013.01); *A23L 1/2364* (2013.01); *A23L 1/307* (2013.01)

(58) Field of Classification Search
CPC ......... A61K 47/00; A61K 47/36; A61K 8/60; A61K 9/0014; A61K 47/26; A61Q 19/00; A61Q 19/10; A23G 1/40; A23G 4/10; A23G 3/42; A23L 1/2364; A23L 1/307
USPC .......................................... 514/777; 549/417
See application file for complete search history.

(56) References Cited

U.S. PATENT DOCUMENTS

| | | | |
|---|---|---|---|
| 1,861,248 | A | 5/1932 | Stebbins |
| 4,846,139 | A | 7/1989 | Devos et al. |

FOREIGN PATENT DOCUMENTS

| | | |
|---|---|---|
| EP | 0189704 B1 | 8/1986 |
| EP | 512910 | 11/1992 |
| EP | 0735042 | 10/1996 |
| EP | 1006128 | 6/2000 |
| EP | 1207164 | 5/2002 |
| EP | 1245582 | 10/2002 |
| WO | 2004067595 | 8/2004 |

OTHER PUBLICATIONS

Sokmen et al, LWT, 2006, 39, 1053-1058.*
International search report dated Oct. 7, 2009 in corresponding PCT/FR2009/050276.

* cited by examiner

*Primary Examiner* — Jason Sims
*Assistant Examiner* — Ibrahim D Bori
(74) *Attorney, Agent, or Firm* — Young & Thompson

(57) ABSTRACT

A crystallized maltitol powder including a maltitol content greater than 99.5% by weight, characterized by a particle-size distribution by volume, determined by laser granulometry, having less than 20% particles less than 200 μm in size, less than 6% particles less than 100 μm in size, less than 2% particles less than 40 μm in size and a pour value less than or equal to 10 seconds, an aerated density greater than 0.85 g/ml, a compacted density greater than 0.97 g/ml, and a compressibility of less than 17%, and to its use in the pharmaceuticals and above all foods sectors, in particular in the formulation of chocolates or table sweeteners.

3 Claims, No Drawings

LARGE PARTICLE SIZE CRYSTALLISED MALTITOL POWDER, METHOD FOR PREPARING SAME AND APPLICATIONS THEREOF, PARTICULARLY IN CHOCOLATE PRODUCTION

The present invention relates to a maltitol powder with a high crystallized maltitol content and having a coarse particle size, practically devoid of fine particles. This crystallized maltitol powder is also characterized by its excellent flowability and its density.

Within the meaning of the invention, by "crystallized maltitol powder" is meant the product of the standard crystallization of an aqueous solution of maltitol.

Within the meaning of the invention, by "high maltitol content" is meant a maltitol content greater than 99.5% by weight, preferably greater than 99.7% by weight, even more preferably greater than 99.8% by weight.

4-O-alpha-D-glucopyranosyl-D-glucitol, commonly called maltitol, is a polyol obtained on an industrial scale by hydrogenation of maltose. It is of great interest because it is chemically more stable, less calorific, and has a lower glycemic index than sucrose, but still advantageously has organoleptic properties very close to those of this sugar. In addition, a characteristic of maltitol is that it is not cariogenic, which opens up for it and has already opened up for it many uses in industry, in particular in the pharmaceutical and food industries, in particular in the fields of chewing gum, table sweeteners and chocolate.

In the field of chocolate, for example, a distinction is drawn between three types of chocolate: dark chocolate, milk chocolate and white chocolate.

In general, a conventional dark chocolate can be defined as a product obtained from cocoa liquor (containing approximately 54% fats), sucrose and cocoa butter. Frequently an emulsifier such as lecithin is also used and also sometimes cocoa powder, and optionally a flavouring.

Milk chocolate further contains milk solids, and white chocolate also contains some but has no defatted dry cocoa powder.

From a physical point of view, a chocolate can be compared to an almost anhydrous dispersion of very fine non-fat particles (sucrose, lactose, proteins, minerals) in a solidified fat phase, comprising essentially triglycerides.

These last-named come exclusively from cocoa in the case of a dark chocolate, but also come from milk in the case of milk or white chocolate.

A standard process for the manufacture of chocolate comprises the following successive essential steps:
 kneading,
 refining,
 optionally dry conching
 wet conching,
 tempering,
 moulding,
 cooling,
 packaging.

The purpose of kneading is to obtain a homogeneous paste from sugar, cocoa paste and optionally cocoa butter and milk powder.

The operation takes place in a mixer. The paste obtained must have a particular texture, suitable for the subsequent refining operation.

It is possible to adjust it by the choice of particle size of the sugar and also through the fat content.

Refining involves rolling the paste obtained, after the kneading step, between steel cylinders, so as to reduce the size of the particles to less than approximately 25 or 30 microns.

This operation transforms the initial paste into fine, hygroscopic powder that is able to trap the ambient odours.

At this stage, it is thus desirable that the conching takes place as quickly as possible.

Conching is essential to modify the flavour and improve the rheological properties of the chocolate.

This operation can take place in a single step (wet conching) or in two steps (dry, then wet, conching) and last from some hours to several days.

The refined powder is hot mixed at around 75-80° C. in the case of a dark chocolate, and at around 65° C. for white and milk chocolates. Dry conching involves carrying out this hot mixing in the absence of high levels of fats. It allows reducing the conching times.

During this operation, the flavour of the chocolate develops. Thanks to the increase in temperature and the aeration of the mass, undesirable compounds such as aldehydes and short fatty acids escape from the mass through volatilization, while other aromatic compounds are formed.

In addition, the rheology of the product changes: the powder obtained at the end of refining becomes pasty. The insoluble particles (of sugar, cocoa, milk) break up through friction and departure of water and round off to give the paste a greater fluidity with a lower flow threshold.

To further improve these characteristics, lecithin is generally added to the chocolate some hours before the end of conching.

This coats the sugared particles and emulsifies the traces of residual water to give the chocolate good flow properties which are essential for the subsequent moulding step.

The chocolate is tempered in order to allow a crystallization of the cocoa butter in a stable form.

For this, the chocolate-flavoured paste is raised to a temperature close to 25 to 27° C., sometimes slightly lower, so as to create crystalline nuclei of every kind, then to a slightly higher temperature during moulding, in order to melt the unstable crystalline forms.

Moulding is an operation which shapes the chocolate, for example in the form of bars or figurines. The chocolates may be solid or filled.

Sucrose has been the reference sweetening filler of the chocolate industry right from the start. Its sensory and technological properties make it particularly suitable for this type of confectionery product.

On the other hand, its nutritional properties may give rise to criticism. Sucrose actually has a calorific value of 4 kcal/g, which gives the chocolate of which sucrose is the essential constituent, a sizable calorific value.

It is also known that sugar is absolutely contra-indicated for diabetics, as the glucose that it contains can be quickly assimilated by the body, which can produce severe hyperglycemia for these patients.

Finally, sucrose is a substrate that can be fermented by the commensal bacteria of the mouth, which convert it into corrosive acids that are the cause of dental caries.

To overcome these drawbacks, consideration has been given to replacing sucrose with polyols in chocolate.

These polyols can be in particular hydrogenated monosaccharides such as sorbitol, mannitol, xylitol, erythritol or hydrogenated disaccharides such as maltitol, lactitol, hydrogenated isomaltulose (equimolecular mixture of glucopyranosyl-1-6 sorbitol and glucopyranosyl 1-1 mannitol).

In the pure state, these polyols have no reductive power and are not fermented by the buccal flora into acids. They thus allow the manufacture of non-cariogenic chocolates inasmuch as the other ingredients of the formulation do not supply fermentable sugars. In the case of milk and white chocolates, the milk can be replaced by lactose-free milk ingredients in order to best ensure this low cariogenicity.

Polyols are slowly metabolized and, after they have been consumed, do not cause a sudden increase in the level of glucose in the blood. Consequently, they are often recommended in the diet of diabetics.

In addition, their calorific value is estimated on average at 2.4 kcal/g (10.0 KJ/g) or approximately 60% that of sugar.

However, the calorific reduction of the currently commercialized chocolates containing polyols still remains limited, for the simple reason that, added to the calorific value of sweetening filler, there is the much greater calorific value of the fats which constitute another essential ingredient of chocolate.

These fats generally come from the cocoa and/or milk.

Their calorific value is actually 9 kcal/g. In addition, they are essentially saturated. Thus they are not particularly recommended by nutritionists and run counter to the current concern of consumers, which is to limit the excessive intake of calories through diet.

To address this concern, in the case of chocolate, sucrose should thus be replaced by a low-calorie substitute, polyols being in particular completely suitable on this score, but the quantity of fats should also be reduced.

However, there are technological manufacturing imperatives including in particular the rheological characteristics necessary to provide good conditions for the refining, conching and moulding operations, which a priori oppose a significant reduction in the fat content in chocolates containing polyols.

The applicant company provided a technical solution to these problems in its patent EP 512,910, which solution rests on the development of a hypocalorific chocolate which, although it had a very low fat content of less than 32% by weight, had technological and organoleptic properties comparable with those of conventional chocolate containing sucrose: using to constitute the sweetening filler products selected from the group consisting of high-purity crystallized maltitol, lactitol, hydrogenated isomaltulose, polymers of low calorie saccharides, or mixtures thereof.

However, by "high-purity crystallized maltitol" was meant in patent application EP 512,910:
crystallized maltitol having a maltitol content expressed as dry/dry weight of at least 92%, preferably of at least 95%, and even more preferably of at least 97%,
such as that obtained according to the manufacturing process described in the European patent EP 189,704 of which the applicant company is the proprietor (the procedure for crystallization in water by cooling is described in the example of the said patent application).

This "high-purity crystallized maltitol" obtained by the applicant company customarily has, for an arithmetic mean diameter comprised between 180 and 230 μm, a particle-size distribution by volume, characterized by:
more than 20% particles less than 200 μm in size,
more than 7% particles less than 100 μm in size,
more than 2% particles less than 40 μm in size (the measurements are determined by laser granulometry, as will be explained below).

This product is also marketed by the applicant company under the brand name MALTISORB® P200.

Although this "high-purity crystallized maltitol" is wholly suitable for use in chocolate, in particular for the manufacture of a low calorie chocolate, the applicant company found that the presence of the fine particles of crystallized maltitol measuring less than 200 μm, more particularly less than 100 μm, and even more particularly less than 40 μm could appear to be prejudicial to the conditions of manufacture of a chocolate with a very low fat content, in particular during the mixing step, before passing through the refining step.

In the field of table sweeteners, the applicant company also provided in its patent EP 1,245,582 fibre-enriched table sweeteners in powder form that can in particular contain polyols.

By table sweeteners are usually meant compositions that replace conventional sugars (sucrose) in powder form which have a sweetening power comparable with or greater than that of sucrose, for a calorific value of the same order (approximately 4 Kcal/g) or even less.

Because their sweetening power is generally greater, the quantities of table sweeteners necessary to sweeten food or drink are thus smaller than those required with sucrose, which further reduces the calorific value for the same sweetening power.

Sweetening power is for example supplied by intense sweetening agents prepared by chemical synthesis such as saccharine, aspartame, acesulphame K, cyclamate, stevioside, sucralose, neotame or alitame.

These table sweeteners also contain, with the sweetening agent, fillers that are usually selected from polyols, such as for example sorbitol, xylitol, mannitol, lactitol, maltitol, erythritol and isomalt taken alone or mixed, or also polysaccharides or oligosaccharides of dextrin, maltodextrin, polydextrose or fructooligosaccharide type.

Table sweeteners are intensively used in the food and catering industries, in particular in powder form, to supply sweet tastes without a high intake of calories.

Such table sweeteners are thus widespread in so-called dietetic or "light" foods, intended for slimming agents or other agents with a controlled calorific value.

In its patent EP 1,245,582, the applicant company proposes fibre-enriched table sweeteners, characterized in that they comprise from 3 to 99%, and preferably 10 to 95% by weight of branched maltodextrins having between 15 and 35% of 1-6 glucoside bonds, a reducing-sugars content of less than 20%, a polymolecularity index of less than 5 and a number-average molecular weight Mn at most equal to 4500 g/mol, and in that they are stable under acid conditions.

By "branched maltodextrins" is meant maltodextrins described in patent application EP 1,006,128 of which the applicant company is also the proprietor.

These branched maltodextrins are of an indigestible nature, what reduces their calorific value, by preventing their assimilation in the small intestine. They thus constitute a source of indigestible fibres.

In its patent EP 1,245,582 the applicant company found that the incorporation of the said branched maltodextrins advantageously allows a partial or total substitution of the fillers in fibre-enriched table sweeteners so as to reduce their cariogenicity, while constituting a supply of indigestible fibres where the fructooligosaccharides or polydextroses customarily used were unable to lay claim.

Thus, by replacing for example all or some of the maltodextrins in a calorific sweetening composition with branched maltodextrins, a composition lightened to 50% of its initial calorific value, having satisfactory organoleptic qualities, can be obtained.

All the compositions described in the patent application EP 1,006,128 are suitable for the preparation of table sweeteners according to the invention.

In addition to the branched maltodextrins and the said intense sweeteners, these fibre-enriched table sweeteners proposed by the applicant company additionally contain polyols.

These polyols are advantageously selected from the group constituting of sucrose, sorbitol, xylitol, mannitol, maltitol, isomalt, lactitol and erythritol, alone or in combination.

According to an advantageous variant, the said fibre-enriched table sweeteners according to the invention comprise from 3 to 50% by weight of the said branched maltodextrins, being made up to 100% by weight by a sugar or a polyol selected from the group constituting of sucrose, fructose, dextrose, maltose, dehydrated glucose syrups, maltitol, lactitol, mannitol, xylitol, sorbitol, erythritol, isomalt, threitol and iditol alone or in combination.

In the particular case of maltitol, the applicant company also found that the presence of fine particles of crystallized maltitol measuring less than 200 μm, more particularly less than 100 μm and even more particularly less than 40 μm could appear to be prejudicial to the conditions of manufacture of the said table sweeteners.

It is also noted that, the higher the concentration of branched maltodextrins, the less easily the crystallized maltitol powder will agglomerate if it is rich in particles having a fine granulometry.

Moreover, the applicant company also found that, for this use as a table sweetener, the flowability and the density of the maltitol powder are important parameters.

All of the above shows that there remains an unsatisfied need to provide a crystallized maltitol powder which on the one hand has a high granulometry practically devoid of fine particles, what allocates it more particularly to the fields of chocolate (in particular chocolate with a low fat content), and on the other hand has a good flowability and a high density, what allocates it more particularly to the field of table sweeteners.

It is to the credit of the applicant company to have succeeded, after thorough research on the subject, in preparing a crystallized maltitol powder which does not have the faults recorded for the known maltitol powders.

The invention consequently relates, firstly, to a crystallized maltitol powder having a maltitol content greater than 99.5% by weight, preferably greater than or equal to 99.7% by weight, more preferably greater than 99.8% by weight, characterized in that:
 the particle-size distribution by volume, determined by laser granulometry, has:
  less than 20%, preferably less than 15%, more preferably less than 10% and even more preferably less than 5% particles less than 200 μm in size,
  less than 6% particles of less than 100 μm in size,
  less than 2% particles of less than 40 μm in size, and
 a pour value less than or equal to 10 seconds, preferably less than or equal to 5 seconds,
 an aerated density greater than 0.85 g/ml, preferably comprised between 0.88 and 1.00 g/ml, a compacted density greater than 0.97 g/ml, preferably comprised between 0.98 et 1.05 g/ml and a compressibility of less than 17%, preferably less than 10%, and even more preferably less than 5%.

The particle-size distribution values are determined on a BECKMAN-COULTER LS 230 LASER type diffraction granulometer fitted with its powder dispersion module (dry route), in accordance to the technical manual and the manufacturer's instructions.

The operating conditions of screw speed under the hopper and vibration intensity of the dispersion chute are determined in such a way that the optical concentration is comprised between 4% and 12%, ideally 8%.

The measurement range of the LS 230 LASER type diffraction granulometer is 0.04 μm to 2,000 μm. The results are calculated in % by volume, and expressed in μm.

The particle-size distribution curve also allows the value of the volume mean diameter (arithmetic mean) D4,3 to be determined.

The crystallized maltitol powder of the invention is mainly characterized by the low proportion of small particles.

More particularly, the very low proportion of particles less than 100 μm in size gives the crystallized maltitol powder according to the invention remarkable flow properties.

The crystallized maltitol powder according to the invention is also characterized by:
 its flowability,
 its density (aerated and compacted) and its compressibility.

The flow values are determined according to the measurement method recommended by the European Pharmacopeia (EP 5.0 volume 1, January 2005: 20916, paragraph 2.9.16; equipment according to Figure 2-9-16-2). Precisely 100 g of powder are poured into the standardized funnel of which the outlet is closed. When this outlet is opened, a chronometer is started then stopped at the end of the flow of the product (empty funnel). The flow measurements are given in seconds.

The aerated and compacted density and compressibility values of the crystallized maltitol powder according to the invention are determined using the PTE type POWDER TESTER apparatus marketed by the company HOSOKAWA, following the manufacturer's instructions.

This apparatus allows the measurement, under standardized and reproducible conditions, of the flowability of a powder by measuring in particular the aerated bulk density and the compacted bulk density and then the calculation of the compressibility values from these data, using the following formula:

$$\text{Compressibility }(\%) = \frac{(\text{compacted density} - \text{aerated density})}{\text{compacted density}} \times 100$$

The crystallized maltitol powder according to the invention is thus firstly characterized by its compacted density and its aerated density, this measurement being carried out on the PTE type POWDER TESTER apparatus, as mentioned above, according to the method recommended in the operating instructions for the said POWDER TESTER (default setting 180 vibrations for the measurement of compacted density).

Under these conditions, the crystallized maltitol powder according to the invention has an aerated density of more than 0.85 g/ml, preferably comprised between 0.88 et 1.00 g/ml, a compacted density of more than 0.97 g/ml, preferably comprised between 0.98 and 1.05 g/ml.

The compressibility value is also a very important factor for characterizing particular properties of the crystallized maltitol powder according to the invention.

According to the operating instructions for the HOSOKAWA PTE apparatus, when the compressibility value is approximately 20%, the powder does not flow freely and tends to form arches in the hopper. For particular compressibility values of 40-50%, it actually becomes impossible to discharge the material from the hopper once the material has been stored there.

The crystallized maltitol powder according to the invention has a compressibility value of less than 17%, preferably less than 10%, and even more preferably less than 5%, which corresponds to a wholly remarkable flow, unlike other crystallized maltitol powders with a higher proportion of fine particles, as will be exemplified below.

These parameters of density, flowability and mean diameter make the crystallized maltitol powder according to the invention particularly suitable for the uses for which it is intended.

A first family of crystallized maltitol powder according to the invention has, for an arithmetic mean diameter D4,3 comprised between 200 and 350 µm, a particle-size distribution by volume with less than 20%, preferably less than 15% of particles of less than 200 µm in size.

A second family of crystallized maltitol powder according to the invention has, for an arithmetic mean diameter D4,3 comprised between 450 and 600 µm, a particle-size distribution by volume with less than 10%, preferably less than 5% of particles of less than 200 µm in size.

The crystallized maltitol powder according to the invention can be obtained using a technique of separating the maltitol crystals according to their size and weight; above all a process allowing the extraction of the fraction of the largest maltitol crystals.

To achieve this result, the applicant company recommends the use of a static separator, more commonly called zig-zag separator by a person skilled in the art (cf. the teaching of U.S. Pat. No. 1,861,248).

The separation in a zig-zag selector is a pneumatic gravity separation. This is a separation process in which the solid particles are separated according to their behaviour during their fall, since they are subjected, in the separation zone, to the force of gravity and the drag force of the airflow. The separation is actually based on the difference in the trajectories of non-identical particles in the separation zone.

In the process according to the invention, a zig-zag separator with several stages is chosen that allows the same air to be used for all the stages, and the separation to be repeated both in the ascending stream of the light particles and in the descending stream of air of the coarse particles.

The separator is constructed by assembling a number of sections together with a fixed angle in order to create the channel of the zig-zag. The channel has a rectangular cross-section. Its particular geometry and the direction of the airflow thus induces two different particle streams: a stream of light particles carried along by the ascending stream of air; a stream of heavy particles descending along the lowest wall of each section.

At each stage, the particles of the two streams are thus subjected to a fresh separation. After this, the particles continue their movements in the stream of original particles or are transported into the stream of opposite direction.

The performance of the separator is determined by the behaviour of the particles at each stage on the one hand and by the interaction between the stages on the other band.

In the process according to the invention, the zig-zag separator used allows a crystallized maltitol powder to be separated into two fractions (fine and coarse).

To do this, an ascending jet of air (primary air) is passed into the zig-zag separator, its speed allowing the cut-off diameter to be characterized.

Particles with a diameter larger than the cut-off diameter fall despite the stream, while the others are carried along by the ascending air.

The process of preparing the crystallized maltitol powder according to the invention can thus comprise for example:
a) feeding a zig-zag separator having a channel composed of several stages having a 120° slope with a crystallized maltitol powder having, an arithmetic mean diameter comprised between 180 and 230 µm, a particle-size distribution by volume of:
more than 20% particles of less than 200 µm in size,
more than 7% particles of less than 100 µm in size,
more than 2% particles of less than 40 µm in size,
b) controlling the flow rate of primary air so as to recover a fraction of crystallized maltitol powder having a particle-size distribution by volume of:
less than 20%, preferably less than 15%, more preferably less than 10% and even more preferably less than 5% particles less than 200 µm in size,
less than 6% particles less than 100 µm in size,
less than 2% particles less than 40 µm in size.

According to a first preferred embodiment of the process according to the invention, the process of preparing the crystallized maltitol powder according to the invention then comprises:
a) feeding a zig-zag separator having a channel composed of 7 stages with a 120° slope, with a width comprised between 2 and 3 cm, a length comprised between 4 and 5 cm and a thickness of 4 cm, with a crystallized maltitol powder having, an arithmetic mean diameter comprised between 180 and 230 µm, a particle-size distribution by volume of:
more than 20% particles of less than 200 µm in size,
more than 7% particles of less than 100 µm in size,
more than 2% particles of less than 40 µm in size, at a flow rate comprised between 400 and 600 g/min,
b) fixing the flow rate of primary air at a value comprised between 2 and 5 $m^3/h$,
c) recovering the fraction of the powder having, for an arithmetic mean diameter comprised between 200 and 350 µm, a particle-size distribution by volume of less than 20%, preferably less than 15% particles of less than 200 µm in size.

According to a second preferred embodiment of the process according to the invention, the preparation process for the crystallized maltitol powder according to the invention then comprises:
a) feeding a zig-zag separator having a channel composed of 7 stages with a 120° slope, with a width comprised between 2 and 3 cm, a length comprised between 4 and 5 cm and a thickness of 4 cm, with a crystallized maltitol powder having, an arithmetic mean diameter comprised between 180 and 230 µm, a particle-size distribution by volume of:
more than 20% particles of less than 200 µm in size,
more than 7% particles of less than 100 µm in size,
more than 2% particles of less than 40 µm in size, at a flow rate comprised between 450 and 550 g/min,
b) fixing the flow rate of primary air at a value comprised between 40 and 50 $m^3/h$,
c) recovering the fraction of the powder having, an arithmetic mean diameter comprised between 450 and 600 µm, a particle-size distribution by volume of less than 10%, preferably less than 5% particles of less than 200 µm in size.

The crystallized maltitol powder according to the invention can advantageously be used in the food industry, for example in the fields of chocolate and table sweeteners.

In the field of chocolate, as will be exemplified below, the quasi-absence of fine particles in the crystallized maltitol powder according to the invention then allows a better fluidity of the mass obtained after mixing, a better transfer to the refining step without impacting on the final rheology of the chocolate thus manufactured.

However, there is nothing to prevent its use for any other purpose, such as for example in the fields of:
- baking (for the topping of pastries such as doughnuts, more particularly for its flowability in dispensing and mixing systems in mixed bakery/cake shop uses, industrial bakeries (ease of dispensing) or industrial-scale pastry manufacture, and for its particle size as a substitute for crystal sugar (in high-fat fillings for example).
- candy-coating of confectionery products (crystallized fruits, gums, jellified products, boiled sweets),
- chewing gums (insertion of coarse crunchy crystals into the centre of the chewing gum),
- fondants,
- pharmaceutical sachets,
- instant preparations,
- carriers for flavourings,
- carriers for intense sweeteners,
- cereals and breakfast cereals (glazed), and
- in sauces without added sugar.

More particularly, the maltitol powder according to the invention, having a mean diameter of the maltitol particles comprised between 450 and 600 μm, will be chosen for uses requiring dry baking mixtures, for the preparation of ice creams, for powdered drinks, for pastry toppings and for confectionery products.

It can also advantageously be used to give a crunchy texture in the mouth.

The invention will be even better understood with the help of the following examples, which are not limitative and merely list some embodiments and some advantageous properties of the crystallized maltitol powder according to the invention.

EXAMPLE 1

MALTISORB® P200 is introduced into the feed hopper of a HOSOKAWA MULTIPLEX ZIGZAG CLASSIFIER 1-40 separator, fitted with 7 stages with a 120° slope, having at each stage a width of 2 cm, a length of 4 cm and a thickness of 4 cm.

Two separation operations are carried out in order to obtain two defined crystallized maltitol powders having respectively:

- a mean diameter of the maltitol particles comprised between 200 and 350 μm (product "A"),
- a mean diameter of the maltitol particles comprised between 450 and 600 μm (product "B").

For this, above all the flow rate of primary air is adapted.

The speed of the ascending air actually defines the cut-off diameter of the initial mixture.

Thus, starting from the same crystallized maltitol powder, here in this case MALTISORB® P200, the use of a primary air flow rate with a value of the order of:
- 3.4 m$^3$/h allows a "defined" crystallized maltitol powder (having of the order of 6% particles of less than 100 μm in size and of the order of 2% particles of less than 40 μm) to be obtained
- 45 m$^3$/h (i.e. a flow rate thirteen times higher) allows the proportion of fine particles of 100 and 40 μm to be further reduced (to 2.1% and 0.7% respectively), but above all the proportion of particles of less than 200 μm in size to be reduced to a remarkable extent (from 19.6% to 5.4%).

The operating conditions are presented in Table 1 below.

TABLE 1

| Maltitol powder according to the invention | Powder flow rate (g/min) | Primary air flow rate (m$^3$/h) | Total weight | Weight fine particles | Weight coarse particles | Feed (μm) Arithmetic mean diameter D (4, 3) | % by volume <40 | % by volume <100 | % by volume <200 | Defined fraction (μm) Arithmetic mean diameter D (4, 3) | % by volume <40 | % by volume <100 | % by volume <200 |
|---|---|---|---|---|---|---|---|---|---|---|---|---|---|
| Product "A" | 500 | 3.4 | 7450 | 3138 | 4312 | 219 | 4.8 | 23.2 | 53.7 | 280 | 2.0 | 6.0 | 19.6 |
| Product "B" | 492 | 45 | 7378 | 450 | 6928 | 219 | 4.8 | 23.2 | 53.7 | 519 | 0.7 | 2.1 | 5.4 |

The flow, aerated and compacted densities and compressibility measurements were carried out using the methods described above.

Product "A" has a flow value of 5 seconds, and also has:
an aerated density of 0.885 g/ml,
a compacted density of 1.025 g/ml, and
a compressibility of 13.655%.

Product "B" has a flow value of 7 seconds, and also has:
an aerated density of 0.96 g/ml,
a compacted density of 0.98 g/ml, and
a compressibility of 2.04%.

EXAMPLE 2

The particle-size distribution of the maltitol in the chocolate is measured by comparing chocolates manufactured with two crystallized maltitol powders according to the invention (Product "A" and Product "B" of Example 1) with those prepared on one hand with sucrose (coarse sugar n° 1-600 from TEREOS), and on the other hand with a crystallized maltitol powder of the prior art recommended for this use, having an arithmetic mean diameter D4,3 comprised between 180 and 230 μm, a particle-size distribution by volume of:
- more than 20% particles of less than 200 μm in size,
- more than 7% particles of less than 100 μm in size,
- more than 2% particles of less than 40 μm in size, such as the MALTISORB® P 200 marketed by the applicant company.

The recipe used for the manufacture of the chocolates is presented in Table 2 below:

TABLE 2

| Chocolate recipe | Composition in % | % fat |
|---|---|---|
| Crystallized maltitol powder according to the invention, or crystallized maltitol MALTISORB ® P200, or coarse sugar 600 | 43.5 | 0.00 |
| Cocoa liquor | 19.5 | 10.53 |
| Cocoa powder | 19.5 | 1.95 |
| Cocoa butter | 17 | 17.000 |
| Lecithin | 0.5 | 0.50 |
| Total | 100 | 29.98 |

The composition is the same for all the tests, only the sweetening agent is different.

The mixing is carried out in a planetary mixer or in a dough mixer, the refining on a three-cylinder grinder.

The pressure between the rolls is as follows:
$1^{st}$ passage: 20-30 bars
$2^{nd}$ passage: 35-45 bars
$3^{rd}$ passage: 55-60 bars.

The composition at the mixing/refining step is given in Table 3 below:

TABLE 3

| | Composition in % | % fat |
|---|---|---|
| Crystallized maltitol powder according to the invention, or crystallized maltitol MALTISORB ® P200, or coarse sugar 600 | 48.1 | 0 |
| Cocoa liquor | 21.55 | 11.64 |
| Cocoa powder | 21.55 | 2.15 |
| Cocoa butter | 8.8 | 8.84 |
| Total | 100 | 22.63 |

The conching is carried out at 60° C. for 14 hours.

The composition at the conching stage is given in Table 4 below:

TABLE 4

| | Composition (%) |
|---|---|
| Powder originating from refining stage | 90.5 |
| Cocoa butter | 9.0 |
| Lecithin | 0.5 |
| Total | 100 |

The crystallized maltitol powders as well as the coarse sugar 600 were characterized by laser granulometry before being used in the chocolate. The particle size measurements were carried out using a BECKMANN COULTER LS 230 laser granulometer.

TABLE 5

| | Arithmetic mean diameter (µm) | % particles measuring less than: | | |
|---|---|---|---|---|
| | | 40 µm | 100 µm | 200 µm |
| MALTISORB ® P200 | 219 | 4.8 | 23.2 | 53.7 |
| Product "A" | 280 | 2.0 | 6.0 | 19.6 |
| Product "B" | 519 | 0.7 | 2.1 | 5.4 |
| Sucrose | 660 | 0.3 | 0.9 | 2.4 |

These results clearly show a very different particle-size distribution between the MALTISORB® P200 and the maltitol powders according to the invention. The particle-size distribution of maltitol powders according to the invention, especially product "B", are closer to the particle-size distribution of sucrose than those of MALTISORB® P200.

The particle size measurements were also carried out on the chocolates (finished products) in order to determine if, after refining and conching, the differences between the MALTISORB® P200, the crystallized maltitol powder of the invention and sucrose persist.

The size of the maltitol particles in the chocolate is determined by any method also known to a person skilled in the art and may, for example, involve dispersing the chocolate broken into pieces in propanol 2, then, in the LS 230 type BECKMAN-COULTER laser diffraction granulometer, selecting the nature of the fluid as being propanol 2 and using the adapted optical model following the manufacturer's instructions.

Table 6 below summarizes the results obtained.

TABLE 6

| | Arithmetic mean diameter (µm) | % particles measuring less than: | | |
|---|---|---|---|---|
| | | 40 µm | 100 µm | 200 µm |
| Chocolates with MALTISORB ® P200 | 13.4 | 96.4 | 99.3 | 100.0 |
| Chocolates with Product "A" | 11.2 | 96.5 | 99.5 | 100 |
| Chocolates with Product "B" | 10.4 | 96.4 | 100.0 | 100.0 |
| Chocolates with sucrose | 15.3 | 90.5 | 99.6 | 100.0 |

The use of the crystallized maltitol powders according to the invention in chocolate gives, after conching, a particle-size distribution fairly close to that obtained with MALTISORB® P200 and sucrose.

This result shows that the refining of the crystallized maltitol powders according to the invention is as effective as that of the MALTISORB® P200 or sucrose.

Next to be studied is the rheological behaviour of the chocolate mass, after mixing and before refining, depending on the particle-size distribution of the tested crystallized maltitol powders.

As the chocolate masses do not flow at this step of the process (the paste is much too thick), the measurement was carried out by penetrometry.

The INSTRON penetration force of the chocolate masses manufactured with the two crystallized maltitol powders according to the invention are measured and, as controls, with the chocolate manufactured with MALTISORB® P200 and sucrose.

The measurements are carried out on a 4502 type INSTRON penetrometer with a 100 N cell, using a spherical piercer 10 mm in diameter. The travel is set at 20 mm, and the traverse speed is 10 mm/min.

The chocolate masses were stored at a temperature of 50° C., and the measurements carried out at this temperature.

The forces were measured at 10 mm penetration.

Table 7 below shows the results obtained, which show that the chocolate mass prepared from the crystallized maltitol powders according to the invention have a much smaller penetration resistance than that prepared from the MALTISORB P200, which indicates a better flow from the mixer to the refining section.

TABLE 7

|  | Force (N) |
|---|---|
| Powder "A" | 0.8 |
| Powder "B" | 0.5 |
| MALTISORB ® P200 | 2.1 |
| Sucrose | 0.4 |

The chocolate mass prepared from the crystallized maltitol powders according to the invention is indeed more mobile, which clearly confirms the impact of the absence of fine particles on the viscosity of the chocolate mass thus prepared. The preparation forces of chocolates manufactured from crystallized maltitol of the invention get closer to the one of the chocolate manufactured with sucrose.

In conclusion, these results show that the rheology of the chocolate, after mixing, is influenced by the particle-size distribution of the crystallized maltitol powder.

Those according to the invention thus allow softer pastes to be obtained than that based on MALTISORB® P200 and closer to the paste based on sucrose.

These pastes will thus be easier to extract from the mixer for their transfer to the later stages of the process (refining, conching).

This result also indicates the possibility of using less fat during mixing (which makes possible a texture identical to the product prepared from MALTISORB® P200), in order to add more free fat at the time of conching, and thus obtain a greater fluidity at the pouring step.

This technological advantage allows a better use of the ingredients during the process of manufacturing chocolate.

The crystallized maltitol powders according to the invention facilitate the first steps of the process of manufacturing chocolate, without modifying the final texture obtained.

Thus, Table 8 shows the rheological characteristics finally measured on the chocolates (after conching).

TABLE 8

|  | Casson viscosity (Pa · s) | Yield point (Pa) |
|---|---|---|
| Chocolate with MALTISORB ® P200 | 3.1 | 51 |
| Chocolate with product "A" | 3.3 | 48 |
| Chocolate with product "B" | 3.1 | 47 |
| Sucrose | 3.7 | 52 |

The differences observed here are not significant, demonstrating a preserved quality of the manufactured chocolates, whichever the sweetening agent used.

EXAMPLE 3

To manufacture table sweeteners, 960 g crystallized maltitol powder of Example 1 (Product "B") is introduced into the tank of an Aeromatic-Fielder AG STREA-1 type laboratory fluidized-air bed granulator-dryer.

The same process is followed with the MALTISORB® P200, used here as control.

A solution of 40 g NUTRIOSE® FB06, 2.2 g of sucralose with 100 g of water is prepared.

The fluidization air of Product "B" like that of the MALTISORB® P200 is heated to 60° C.

The prepared solution is sprayed at a rate of 300 ml/h using a nozzle positioned at the top of the tank.

The spraying is followed by drying for 30 minutes at 60° C. The results obtained are shown in Table 9 below.

TABLE 9

| Maltitol powder tested | Product "B" | MALTISORB ® P 200 |
|---|---|---|
| Aerated density (g/ml) | 0.8 | 0.61 |
| Compacted density (g/ml) | 0.83 | 0.65 |
| Compressibility (%) | 3.6 | 6.1 |
| Appearance | crystals | granules |

It can be noted that the density values of the preparations remain advantageously high with the crystallized maltitol powder according to the invention (>0.75 g/ml for the aerated density) compared with ~0.60 g/ml for the MALTISORB® P200.

Differences in compressibility are also observed: less compaction for the preparations based on crystallized maltitol powder according to the invention, which makes them much more fluid and easier to handle.

As regards the manufacturing operation, it is noted that during the process of granulation of the crystallized maltitol powder according to the invention with NUTRIOSE® FB06, fluidization is promoted in the fluidized-air bed granulator, as the mixture is more homogeneous than with the MALTISORB® P200.

In addition, a clearly better productivity is observed, as there is less loss of material due to the fine particles sticking to the filters and the walls of the equipment.

Finally, the appearance of the table sweeteners manufactured from MALTISORB® P200 is closer to that of granules, whereas that of the table sweeteners prepared from the maltitol powder according to the invention is more that of a monocrystal (appearance wholly similar to large sucrose crystals).

The visual perception of the table sweeteners prepared from the maltitol powder according to the invention is thus clearly better, and allows one of the key objectives of the perception of intense sweeteners by consumers to be achieved: that of making the end-users forget that they are using intense sweeteners.

The invention claimed is:

1. A process of preparing a crystallized maltitol powder comprising:
    a) feeding a zig-zag separator having a channel composed of several stages with a 120° slope with a crystallized maltitol powder having, for an arithmetic mean diameter comprised between 180 and 230 µm, a particle-size distribution by volume of:
        more than 20% particles of less than 200 µm in size,
        more than 7% particles of less than 100 µm in size, and
        more than 2% particles of less than 40 µm in size;
    b) controlling the flow rate of primary air so as to recover a fraction of crystallized maltitol powder comprising particles less than 200 µm and having a particle-size distribution by volume of:
        less than 20% particles of less than 200 µm in size,
        less than 6% particles of less than 100 µm in size, and
        less than 2% particles of less than 40 µm in size.

2. A process of preparing a crystallized maltitol powder comprising:

a) feeding a zig-zag separator having a channel composed of several stages with a 120° slope with crystallized maltitol powder having, for an arithmetic mean diameter comprised between 180 and 230 μm, a particle-size distribution by volume of:
more than 20% particles of less than 200 μm in size,
more than 7% particles of less than 100 μm in size, and
more than 2% particles of less than 40 μm in size;
b) controlling the flow rate of primary air so as to recover a fraction of the crystallized maltitol powder comprising particles less than 200 μm, wherein,
the zig-zag separator has a channel composed of 7 stages with a 120° slope, with a width comprised between 2 and 3 cm, a length comprised between 4 and 5 cm and a thickness of 4 cm,
the crystallized maltitol powder is fed into the zig-zag separator at a flow rate comprised between 400 and 600 g/min,
the flow rate of primary air is fixed at a value comprised between 2 and 5 m$^3$/h, and
the fraction of the powder recovered has, for an arithmetic mean diameter comprised between 200 and 350 μm, a particle-size distribution by volume of less than 20% particles of less than 200 μm in size, less than 6% particles of less than 100 μm in size, and less than 2% particles of less than 40 μm in size.

3. A process of preparing a crystallized maltitol powder comprising:

a) feeding a zig-zag separator having a channel composed of several stages with a 120° slope with a crystallized maltitol powder having, for an arithmetic mean diameter comprised between 180 and 230 μm, a particle-size distribution by volume of:
more than 20% particles of less than 200 μm in size,
more than 7% particles of less than 100 μm in size, and
more than 2% particles of less than 40 μm in size;
b) controlling the flow rate of primary air so as to recover a fraction of the crystallized maltitol powder comprising particles less than 200 μm, wherein,
the zig-zag separator has a channel composed of 7 stages with a 120° slope, with a width comprised between 2 and 3 cm, a length comprised between 4 and 5 cm and a thickness of 4 cm,
the crystallized maltitol powder is fed into the zig-zag separator at a flow rate comprised between 450 and 550 g/min,
the flow rate of primary air is fixed at a value comprised between 40 and 50 m$^3$/h,
the fraction of the powder recovered has, for an arithmetic mean diameter comprised between 450 and 600 μm, a particle-size distribution by volume with less than 10% particles of less than 200 μm in size, less than 6% particles of less than 100 μm in size, and less than 2% particles of less than 40 μm in size.

* * * * *